US00PP13420P3

(12) United States Plant Patent
Cammarota

(10) Patent No.: US PP13,420 P3
(45) Date of Patent: Dec. 24, 2002

(54) PHLOX PLANT NAMED 'COTTON CANDY'

(76) Inventor: Thomas Cammarota, 2541 City View St., Eugene, OR (US) 97405

( * ) Notice: Subject to any disclaimer, the term of this patent is extended or adjusted under 35 U.S.C. 154(b) by 0 days.

(21) Appl. No.: 09/800,866

(22) Filed: Mar. 7, 2001

(65) Prior Publication Data

US 2002/0129419 P1 Sep. 12, 2002

(51) Int. Cl.[7] ..... A01H 5/00

(52) U.S. Cl. ..... Plt./320

(58) Field of Search ..... Plt./320

*Primary Examiner*—Bruce R. Campell
*Assistant Examiner*—W C Haas
(74) *Attorney, Agent, or Firm*—Mark P. Bourgeois

(57) ABSTRACT

A new cultivar of Phlox plant named 'Cotton Candy' that is characterized by prolific blooming, white flowers, a tall and vigorous growth habit, uniformity in containers, and light green leaves. In combination these traits distinguish the new cultivar from all other existing varieties of Phlox.

2 Drawing Sheets

BOTANICAL CLASSIFICATION

Phlox subulata 'Cotton Candy'.

CROSS-REFERENCES TO RELATED APPLICATIONS

The application for Phlox 'Cotton Candy' will be co-pending with another application entitled Phlox Plant Named 'Bubble Gum', U.S. patent application Ser. No. 09/801,205, having the same inventor and filing date as the present invention.

BACKGROUND OF THE INVENTION

The present invention relates to a new and distinct cultivar of Moss Phlox known botanically as *Phlox subulata* (not patented) and hereinafter referred to by the cultivar name 'Cotton Candy'. In 1998 the new cultivar was discovered by the inventor, in a cultivated area of Albany, Oreg. 'Cotton Candy' was a spontaneously occurring sport that was discovered as a branch on *Phlox subulata* 'Candy Stripe', (not patented).

'Cotton Candy' is characterized by uniformity in containers, prolific blooming, vigor, and a tall profile with white flowers held on long stems above the foliage. 'Cotton Candy' is distinguished from the parent plant 'Candy Stripe' by light green foliage and white flowers. It differs from 'White Delight' (unpatented) by its vigor, abundance of flowers, tall flowers, short coarse leaves, and uniformity in containers.

After the sport was observed for performance over a period of months, 'Cotton Candy' was propagated in a cultivated area of Albany, Oreg. The first asexual propagation was accomplished by the inventor in 1998, using vegetative cuttings. The distinguishing characteristics have been determined stable and are reproduced true to type in successive generations.

SUMMARY OF THE INVENTION

The following traits have been repeatedly observed and represent the characteristics of the new cultivar. These attributes in combination distinguish this cultivar from all other commercial varieties. 'Cotton Candy' has not been tested under all possible conditions and phenotypic differences may be observed with variations in environmental, climatic, and cultural conditions, however, without any variance in genotype.

1. 'Cotton Candy' is uniform in containers.
2. 'Cotton Candy' is tall with flowers held above foliage.
3. 'Cotton Candy' is a prolific bloomer.
4. 'Cotton Candy' is vigorous in growth.
5. 'Cotton Candy' has white flowers.
6. 'Cotton Candy' has short, coarse, light green leaves.
7. 'Cotton Candy' is hardy to USDA Zone 3.

BRIEF DESCRIPTION OF THE DRAWINGS

The accompanying color photographs illustrate the distinguishing traits of the new cultivar.

The first drawing sheet shows the entire plant with blooms and foliage from a side perspective.

The second drawing sheet is a close-up of a 'Cotton Candy' flower and bud in the lower photograph and a close-up of a 'Candy Stripe' flower and bud in the upper photograph. All photographs are taken of plants grown in two-gallon containers. The photographs are made using conventional photographic techniques and although flower and foliage colors in the photographs may appear different from the actual colors due to light reflectance, they are as accurate as possible by conventional photography.

BOTANICAL DESCRIPTION OF THE PLANT

The following is a detailed botanical description of the new Phlox cultivar 'Cotton Candy'. Observations, measurements, values, and comparisons were collected in Arroyo Grande Calif., from 12 month old plants grown in two-gallon nursery containers respectively. The plants were grown outdoors with full sun in the morning and then partial shade in the afternoon. The plants were grown in loose well drained soil with a time release fertilizer and were moderately watered. Color determinations are made in accordance with The Royal Horticultural Society Colour Chart from London England, except where general color terms of ordinary dictionary significance are used. The growing requirements of the new variety are similar to the species and there are no known growing problems.

Botanical classification: *Phlox subulata* 'Cotton Candy'.
Common name: Moss Phlox.
Parentage: 'Cotton Candy' was a spontaneously occurring sport, discovered as a branch on the parent plant *Phlox subulata* 'Candy Stripe'.
Propagation: By soft stem cuttings or division.
Rooting habit: Vigorous, fibrous and well branched.
Time to initiate roots: Approximately 21 days at temperatures of 25 degrees Centigrade for roots to develop from an initial cutting.
Crop time: Approximately 24 to 36 weeks to produce a finished plant in a one gallon container from an unrooted cutting.
Plant habit: Spreading habit.
Use: Used as a groundcover, border plant and in rock gardens.
Type: Perennial.
Growth rate: Vigorous growth rate.
Height: Soil level to top of leaves is approximately 7 cm. and soil level to top of flowers is approximately 10 cm. in height.
Width: 40 cm. in width.
Hardiness: USDA Zone 3.
Stem:
*Stem color.*—A combination of 144A,B.
*Stem shape.*—Cylindrical in shape.
*Internode length.*—2.5 cm. in length between nodes.
*Stem width.*—2 mm. in width.
*Stem length.*—7–8 cm. in length.
*Stem surface.*—Pilose surface.
*Branching habit.*—Freely branching and dense.
Foliage:
*Leaf arrangement.*—Opposite.
*Leaf division.*—Simple.
*Leaf shape.*—Narrow, linear.
*Leaf length.*—1.5–2 cm. in length.
*Leaf width.*—2.5–3 mm. in width.
*Leaf apex.*—Apiculate.
*Leaf base.*—Truncate.
*Leaf venation.*—Only mid-vein visible and slightly depressed on adaxial surface, while protruding on abaxial surface.
*Vein color.*—143B.
*Margin type.*—Entire with margins slightly involute.
*Leaf surface.*—Abaxial and adaxial surfaces generally glabrous with hairs at margins and base.
*Petiole.*—Sessile attachment.
*Young leaf color.*—Adaxial and abaxial surfaces are 143B–C.
*Mature leaf color.*—Adaxial and abaxial surfaces are 138A.
*Foliar fragrance.*—Slightly grass-like.
Flower:
*Sexuality.*—Monoclinus.
*Flowering season.*—Early to mid-spring. Plants may flower in summer as well.
*Flower arrangement.*—Usually two single flowers each with a secondary peduncle, on a primary peduncle held upright and above foliage.
*Flower form.*—Corymb.
*Quantity of flowers.*—Six flowers per corymb.
*Flower shape.*—Explanate.
*Fragrance.*—Somewhat spicy.
*Determinate or in determinate.*—Determinate.
*Flowering time.*—Diurnal.
*Flower aspect.*—Outward aspect.
*Flower diameter.*—2 cm. in diameter.
*Flower depth* (*corolla tube*).—1.75 cm. in depth.
*Peduncle length.*—8–9 mm. in length.
*Peduncle width.*—1 mm. in width.
*Angle of peduncle to stem.*—45 degree angle to stem.
*Peduncle color.*—144 A.
*Petals.*—Five in number.
*Petal length.*—9 mm. in length.
*Petal width.*—8 mm. in width.
*Fused or unfused.*—Unfused petals.
*Petal color* (*open, mature*).—156D with light violet markings 77A in the center of the flower encircling the opening to the throat.
*Petal shape.*—Oblong shape.
*Petal margin.*—Entire margin.
*Petal surface.*—Glabrous surface.
*Petal texture.*—Satiny texture.
*Bud shape.*—Oval shape.
*Color of bud.*—Close to 157C but purer white.
*Dimensions of bud.*—8–9 mm. in length and 2 mm. in width.
*Calyx shape.*—Tubular with sepals fused at base.
*Calyx dimensions.*—9 mm. in length and 5–6 mm. in width.
*Sepals.*—Five in number.
*Sepal shape.*—Linear shape.
*Sepal apex.*—Acuminate.
*Sepal color.*—144A.
*Sepal surface.*—Pubescent with soft short hairs.
*Sepal dimensions.*—1.5 mm. in width and 9 mm. in length.
Reproductive organs:
*Stamens.*—Three in number, included and attached to inside of corolla tube.
*Stamen dimensions.*—Less than 1 mm in width and 12 mm. in length.
*Stamen color.*—155C.
*Anthers.*—Versatile.
*Anther dimensions.*—Less than 1 mm. in width and less than 1 mm. in length.
*Anther color.*—18A.
*Pollen color.*—18A.
*Pollen quantity.*—Low to moderate amount of pollen.
*Ovary color.*—144B.
*Ovary position.*—Superior.
*Ovary shape.*—Tumescent.
*Ovary dimensions.*—1 mm. in height and 1 mm in width.
*Pistil shape.*—Slender and filiform.
*Pistil dimensions.*—7 mm. in length and less than 1 mm. in width.
*Pistil color.*—155C.
*Stigma shape.*—Trifid.
*Stigma color.*—155C.
*Stigma dimensions.*—Less than 1 mm. in width and less than 1 mm. in length.
*Style dimensions.*—5 mm. in length and less than 1 mm. in width.
*Style color.*—155C.
Seed: Seed production is rarely observed and has not been observed by the inventor.
Disease resistance: Susceptible to downy mildew.

I claim:

1. A new and distinct cultivar of *Phlox subulata* plant named 'Cotton Candy' as described and illustrated.

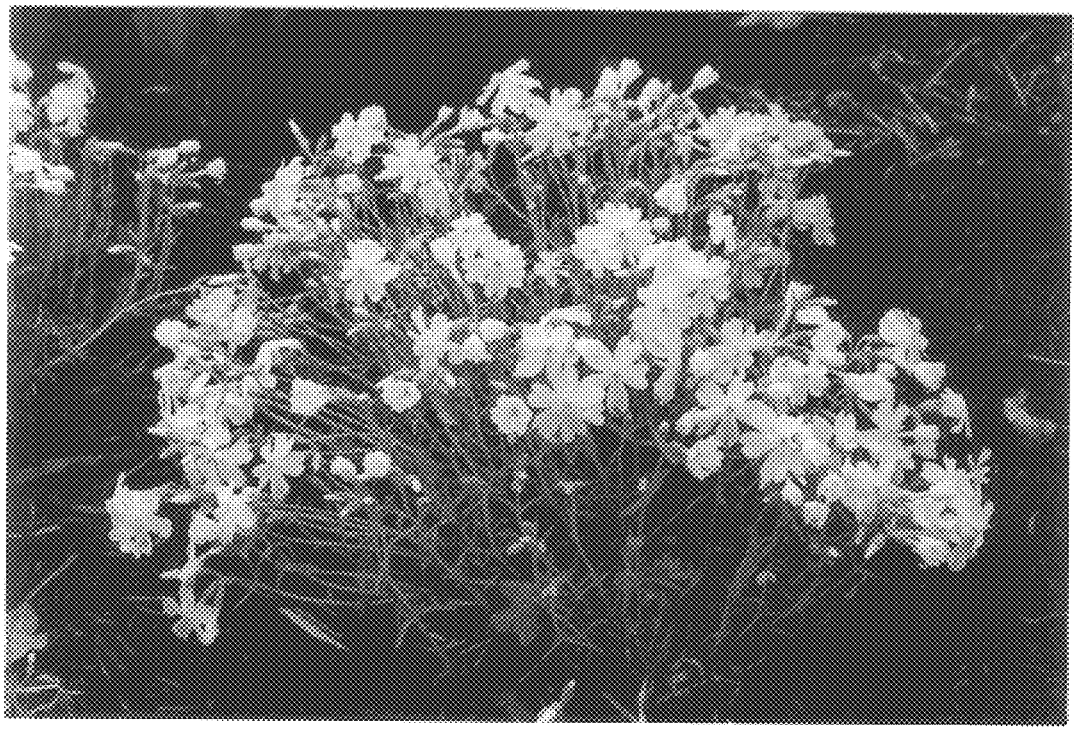

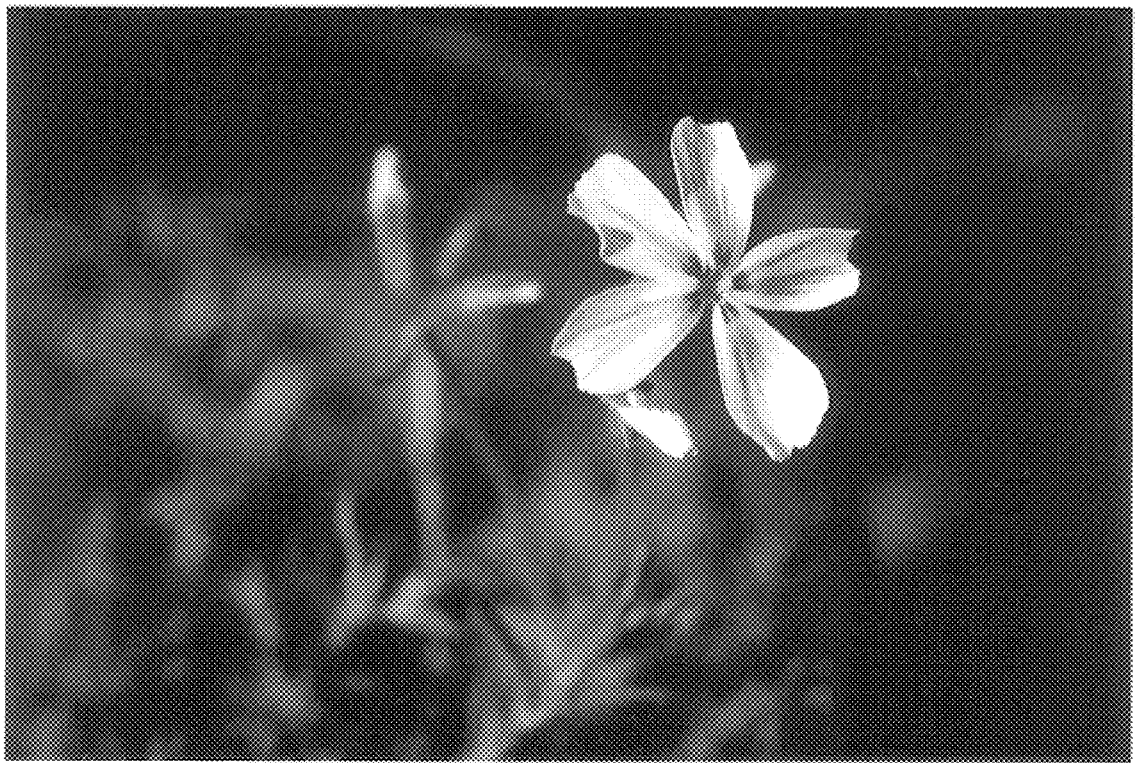
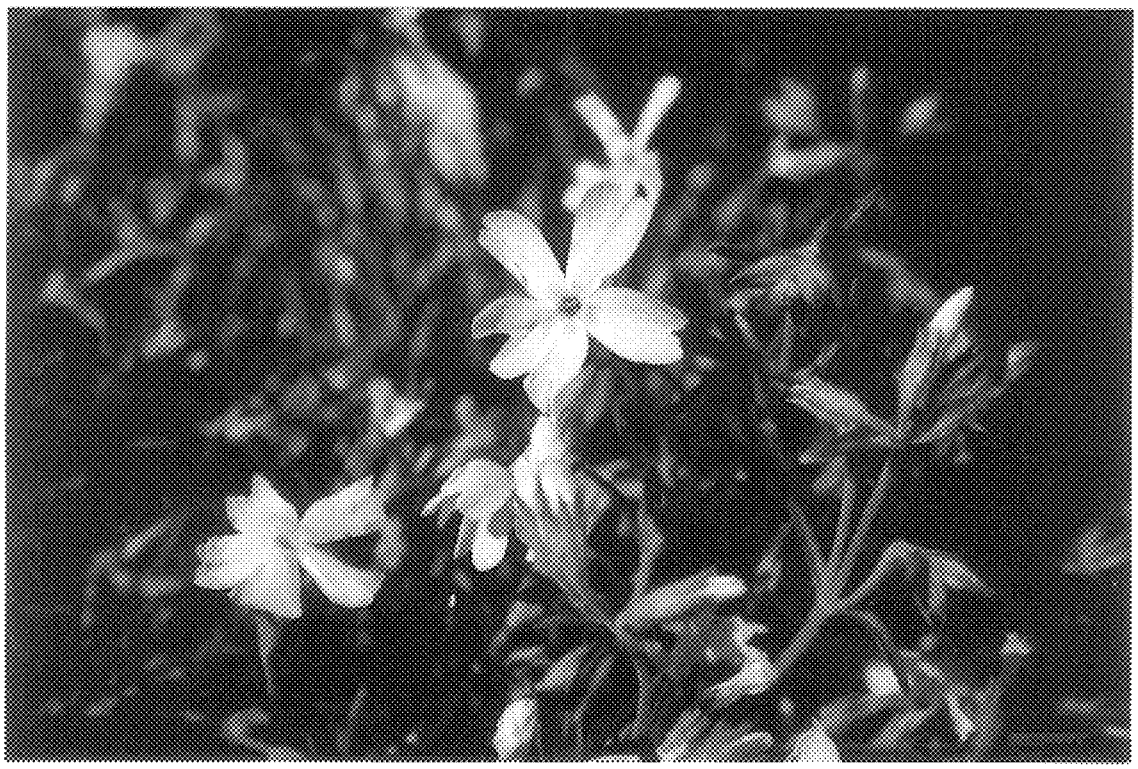

* * * * *